United States Patent [19]

ter Huurne et al.

[11] Patent Number: 6,007,825
[45] Date of Patent: *Dec. 28, 1999

[54] *SERPULINA HYODYSENTERIAE* VACCINE COMPRISING A TLY GENE MUTANT

[75] Inventors: Agnes ter Huurne; Susie Jane Muir, both of Weesp, Netherlands

[73] Assignee: American Cyanamid Company, Madison, N.J.

[ * ] Notice: This patent is subject to a terminal disclaimer.

[21] Appl. No.: 09/186,287

[22] Filed: Nov. 5, 1998

Related U.S. Application Data

[63] Continuation of application No. 08/950,433, Oct. 15, 1997, Pat. No. 5,882,655, which is a continuation of application No. 08/461,748, Jun. 5, 1995, abandoned, which is a continuation of application No. 08/194,127, Feb. 9, 1994, abandoned, which is a continuation of application No. 07/996,197, Dec. 23, 1992, abandoned.

[30] Foreign Application Priority Data

Dec. 23, 1991 [NL] Netherlands ............... EP-91203384.2

[51] Int. Cl.⁶ .................................................. A61K 39/00
[52] U.S. Cl. .................. 424/262.1; 435/69.1; 424/265.1
[58] Field of Search ................................. 435/69.3, 69.1; 424/265.1, 199.1

[56] References Cited

U.S. PATENT DOCUMENTS

| | | | |
|---|---|---|---|
| 4,152,413 | 5/1979 | Goodnow | 424/16 |
| 4,152,415 | 5/1979 | Harris et al. | 424/16 |
| 4,203,968 | 5/1980 | Harris et al. | 424/92 |
| 4,748,019 | 5/1988 | Lysons | 424/92 |
| 4,789,544 | 12/1988 | Nelson et al. | 424/92 |
| 5,017,478 | 5/1991 | Cashion et al. | 435/69.1 |
| 5,176,910 | 1/1993 | McCaman et al. | 424/92 |
| 5,281,416 | 1/1994 | Coloe | 424/92 |
| 5,364,774 | 11/1994 | Muir et al. | 435/69.3 |
| 5,674,500 | 10/1997 | Peeters et al. | 424/199.1 |
| 5,698,394 | 12/1997 | Derhamel et al. | 435/6 |

OTHER PUBLICATIONS

R.J. Lysons, et al, "A Cytotoxic Haemolysin from Treponema *Hyodysenteriae*: A Virulence Factor for Swine Dysentery", *Clinical and Molecular Aspects of Anaerobes*, 25, (1990) pp. 147–151.

K.A. Kent, et al, "Produaction, Purifiction and Molecular Weight Determination of *the Haemolysin of Treponema Hyodysenteriae*", *Med. Microbiology*, vol. 27 (1988), pp. 215–224.

Huurne, et al, "Inactivation of *Serpula (Treponema) Hyodysenteriae*, Hemolysin Gene by Homologous Recombination: Importance of the Hemolysin in Pathogenesis of S. Hyodysenteriae in Mice", *FEMS Microbiology letters*, 92 (1992) pp. 109–114.

Muir, S. et al, May 13–17, 1990; Abs. Annual. Meet. Am. Soc. of Microbiol, vol. 90(0), 1990, p. 46, #B118.

Sambrook et al, Molecular Cloning, Cold Spring Harbor Laboratory Press, 1989, Chapter 15.

Lemcke et al, J. Med. Microbiol., vol. 15, pp. 205–214, 1982.

Goebel et al, J. Bact., Sep. 1982, p. 1290–1298, vol. 151(3).

Goebel et al, Genetic Manipulation:Impact on Man & Society, 1983.

Lysons et al, J. Med. Microbiol, vol. 34, 1991, pp. 97–102.

Muir et al, Infect & Immunity, Feb. 1992, p 529–535 vol. 60(2).

MPSearch, u–embl 143–89 Sequence Search, Result #1, Submission date Aug. 28, 1991.

Goebel et al in Genetic Manipulation: Impact on Man & Society (PAP: COGENE Symp. Meeting date 1983) pp. 29–42 edited by W. Arber et al, ICSU Press Cambridge.

Sambrook et al Molecular Cloning: A Laboratory Manual 2ⁿᵈ Edition Cold Spring Harbor Laboratory CSH, NY (1989) pp.

*Primary Examiner*—James C. Housel
*Assistant Examiner*—Ginny Allen Portner
*Attorney, Agent, or Firm*—Stevens, Davis, Miller & Mosher, L.L.P.

[57] ABSTRACT

According to the present invention a vaccine can be prepared containing a mutant *Serpulina hyodysenteriae* which is defective in its production of biologically active hemolysin. The mutation by which *Serpulina hyodysenteriae* is made defective in its production of hemolytically active hemolysin is established by means of genetical engineering techniques. Such mutations comprise e.g. deletion of part or the entire gene coding for hemolysin and/or nucleotide sequences controlling the production of hemolysin, or insertion of an extra nucleotide or polynucleotide into the gene encoding hemolysin and/or the nucleotide sequences controling the production of hemolysin, or a combination of said deletion and insertion. These vaccines are useful in the prevention of Serpulina infections in susceptible animals such as swine.

11 Claims, 1 Drawing Sheet

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1498 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: SERPULINA HYODYSENTERIAE
      (B) STRAIN: B 204
      (H) CELL LINE: E. COLI JM105 (pJBA) [CBS 512.91]

(ix) FEATURE:
      (A) NAME/KEY: CDS
      (B) LOCATION: 1..456
      (D) OTHER INFORMATION: /product= "UNKNOWN PROTEIN"

(ix) FEATURE:
      (A) NAME/KEY: intron
      (B) LOCATION: 457..470

(ix) FEATURE:
      (A) NAME/KEY: CDS
      (B) LOCATION: 471..1190
      (D) OTHER INFORMATION: /product= "HEMOLYSIN PROTEIN"

(ix) FEATURE:
   (A) NAME/KEY: intron
   (B) LOCATION: 1191..1498

(xi) SEQUENCE DESCRIPTION: SEQ ID NO:1:

```
GAT CCT AAT GCT GAT ACT GAT GAA TCT CCT GCT TTA TTG ATT TCT GCT        48
Asp Pro Asn Ala Asp Thr Asp Glu Ser Pro Ala Leu Leu Ile Ser Ala
 1               5                  10                  15

TCT ATA ACT GAT ACT GAT ACA GTT AAA GTA ATA TTA CAG GCA TTT GCT        96
Ser Ile Thr Asp Thr Asp Thr Val Lys Val Ile Leu Gln Ala Phe Ala
                 20                  25                  30

GAA GAT GTT ACT GAT GAT ATT TAT ACA ATT GGC GGT AAT TTA TGC TAT       144
Glu Asp Val Thr Asp Asp Ile Tyr Thr Ile Gly Gly Asn Leu Cys Tyr
             35                  40                  45

ATA AAA GAT TCT ATA TTA TAT ATT TCT GAT AAT TCT AAT GTT ATA GAT       192
Ile Lys Asp Ser Ile Leu Tyr Ile Ser Asp Asn Ser Asn Val Ile Asp
 50                  55                  60

TCT ATA ATT AAT GGT GAA AAG CCA GCA ACA GCA TTA TCT GCT GAT AAA       240
Ser Ile Ile Asn Gly Glu Lys Pro Ala Thr Ala Leu Ser Ala Asp Lys
 65                  70                  75                  80

GTT GAA ATA GCT AAA AAT AAT ACT ATG GCT TTA TAT TTA GAG TTT AAT       288
Val Glu Ile Ala Lys Asn Asn Thr Met Ala Leu Tyr Leu Glu Phe Asn
                 85                  90                  95

TCT AAT TTA TCA TTA TAT GGT ATT GGA GAT GAA TAT ACT GAA ACT TTT       336
Ser Asn Leu Ser Leu Tyr Gly Ile Gly Asp Glu Tyr Thr Glu Thr Phe
                100                 105                 110

GAA TCA GTT TAT ATA ACT TCA AAT ATA TTA GAA AGC AAT CAT ACT CAA       384
Glu Ser Val Tyr Ile Thr Ser Asn Ile Leu Glu Ser Asn His Thr Gln
            115                 120                 125

ATG CTT TTA AAA GTA AAT ATG AGA GAT AAA GAA AGA AAT TCT CTT TCT       432
Met Leu Leu Lys Val Asn Met Arg Asp Lys Glu Arg Asn Ser Leu Ser
        130                 135                 140

ATA ATA AAA TCT TTC CTT GGA TTA TAATACTAAT ATAA ATG CGA TTA GAT       482
Ile Ile Lys Ser Phe Leu Gly Leu                  Met Arg Leu Asp
145                 150                           1

GAA TAT GTG CAT AGT GAA GGC TAT ACA GAA AGC AGA TCT AAA GCA CAG       530
Glu Tyr Val His Ser Glu Gly Tyr Thr Glu Ser Arg Ser Lys Ala Gln
 5                  10                  15                  20

GAT ATA ATA CTA GCC GGT TGT GTT TTT GTT AAT GGA GTA AAG GTA ACT       578
Asp Ile Ile Leu Ala Gly Cys Val Phe Val Asn Gly Val Lys Val Thr
                 25                  30                  35

TCT AAG GCT CAT AAA ATA AAA GAT ACT GAT AAT ATA GAA GTT GTT CAG       626
Ser Lys Ala His Lys Ile Lys Asp Thr Asp Asn Ile Glu Val Val Gln
             40                  45                  50

AAT ATA AAA TAT GTA TCA AGA GCT GGA GAA AAA TTA GAA AAG GCG TTT       674
Asn Ile Lys Tyr Val Ser Arg Ala Gly Glu Lys Leu Glu Lys Ala Phe
 55                  60                  65

GTA GAA TTT GGA ATA TCT GTA GAA AAT AAA ATA TGT TTA GAT ATA GGA       722
Val Glu Phe Gly Ile Ser Val Glu Asn Lys Ile Cys Leu Asp Ile Gly
         70                  75                  80

GCT TCT ACA GGA GGA TTT ACA GAT TGT CGT CTT AAG CAT GGT GCT AAA       770
Ala Ser Thr Gly Gly Phe Thr Asp Cys Arg Leu Lys His Gly Ala Lys
 85                  90                  95                 100

AAA GTT TAT GCT CTT GAT GTA GGA CAT AAT CAG CTA GTT TAT AAA CTT       818
Lys Val Tyr Ala Leu Asp Val Gly His Asn Gln Leu Val Tyr Lys Leu
                105                 110                 115

CGT AAT GAT AAT AGG GTA GTG TCA ATA GAA GAT TTC AAT GCC AAA GAT       866
Arg Asn Asp Asn Arg Val Val Ser Ile Glu Asp Phe Asn Ala Lys Asp
                120                 125                 130

ATA AAT AAA GAA ATG TTC AAT GAT GAA ATC CCA TCT GTA ATA GTA AGT       914
Ile Asn Lys Glu Met Phe Asn Asp Glu Ile Pro Ser Val Ile Val Ser
```

```
                    135                 140                 145
GAC GTA TCA TTT ATA TCA ATA ACA AAA ATA GCA CCA ATC ATA TTT AAA      962
Asp Val Ser Phe Ile Ser Ile Thr Lys Ile Ala Pro Ile Ile Phe Lys
    150                 155                 160

GAA TTA AAT AAT TTA GAG TTT TGG GTA ACT TTA ATA AAA CCA CAA TTT     1010
Glu Leu Asn Asn Leu Glu Phe Trp Val Thr Leu Ile Lys Pro Gln Phe
165                 170                 175                 180

GAA GCT GAA AGA GGT GAT GTT TCA AAA GGC GGT ATA ATA CGA GAT GAT     1058
Glu Ala Glu Arg Gly Asp Val Ser Lys Gly Gly Ile Ile Arg Asp Asp
                185                 190                 195

ATA CTT AGA GAA AAA ATA TTA AAT AAT GCT ATT TCA AAG ATA ATA GAC     1106
Ile Leu Arg Glu Lys Ile Leu Asn Asn Ala Ile Ser Lys Ile Ile Asp
                    200                 205                 210

TGC GGA TTT AAA GAA GTT AAT AGA ACC ATC TCT CCT ATA AAA GGT GCT     1154
Cys Gly Phe Lys Glu Val Asn Arg Thr Ile Ser Pro Ile Lys Gly Ala
                215                 220                 225

AAA GGT AAT ATA GAA TAT TTA GCT CAT TTT ATT ATT TAATCATTTT          1200
Lys Gly Asn Ile Glu Tyr Leu Ala His Phe Ile Ile
    230                 235                 240

CTATTTTATG TGTATTTCTC TGTTTATATA TTTCATATTC TTTATAGAAG CCTTCTACAT   1260

CATTTACCAT TAAATATCCT TCTTCTGATA TATCTAATGA TTTTATTTTT AATATTTCAT   1320

TTTCTACATT ACTTTTATAT TCTATGCCTA TCATAGAACA AATATCATTT ATATTATATT   1380

GAAATTTTAT TTTGTTTATA TTTTTGAATA AAAGTTCAGT TTTTATTAAC GCTTCTATTA   1440

TTATCACGAA TTTGCTTACT ACTTTATTAG CATTAAAAGA CCTTATTCTA GAAATAGT    1498

(2) INFORMATION FOR SEQ ID NO:2:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:2:

Asp Pro Asn Ala Asp Thr Asp Glu Ser Pro Ala Leu Leu Ile Ser Ala
1               5                   10                  15

Ser Ile Thr Asp Thr Asp Thr Val Lys Val Ile Leu Gln Ala Phe Ala
                20                  25                  30

Glu Asp Val Thr Asp Asp Ile Tyr Thr Ile Gly Gly Asn Leu Cys Tyr
            35                  40                  45

Ile Lys Asp Ser Ile Leu Tyr Ile Ser Asp Asn Ser Asn Val Ile Asp
50                  55                  60

Ser Ile Ile Asn Gly Glu Lys Pro Ala Thr Ala Leu Ser Ala Asp Lys
65                  70                  75                  80

Val Glu Ile Ala Lys Asn Asn Thr Met Ala Leu Tyr Leu Glu Phe Asn
                85                  90                  95

Ser Asn Leu Ser Leu Tyr Gly Ile Gly Asp Glu Tyr Thr Glu Thr Phe
                100                 105                 110

Glu Ser Val Tyr Ile Thr Ser Asn Ile Leu Glu Ser Asn His Thr Gln
            115                 120                 125

Met Leu Leu Lys Val Asn Met Arg Asp Lys Glu Arg Asn Ser Leu Ser
    130                 135                 140

Ile Ile Lys Ser Phe Leu Gly Leu
145                 150

(2) INFORMATION FOR SEQ ID NO:3:
```

(i) SEQUENCE CHARACTERISTICS:
    (A) LENGTH: 240 amino acids
    (B) TYPE: amino acid
    (D) TOPOLOGY: linear (ii) MOLECULE TYPE: protein (xi) SEQUENCE DESCRIPTION: SEQ ID NO:3:

```
Met Arg Leu Asp Glu Tyr Val His Ser Glu Gly Tyr Thr Glu Ser Arg
 1               5                  10                  15

Ser Lys Ala Gln Asp Ile Ile Leu Ala Gly Cys Val Phe Val Asn Gly
            20                  25                  30

Val Lys Val Thr Ser Lys Ala His Lys Ile Lys Asp Thr Asp Asn Ile
            35                  40                  45

Glu Val Val Gln Asn Ile Lys Tyr Val Ser Arg Ala Gly Glu Lys Leu
        50                  55                  60

Glu Lys Ala Phe Val Glu Phe Gly Ile Ser Val Glu Asn Lys Ile Cys
 65                  70                  75                  80

Leu Asp Ile Gly Ala Ser Thr Gly Gly Phe Thr Asp Cys Arg Leu Lys
                85                  90                  95

His Gly Ala Lys Lys Val Tyr Ala Leu Asp Val Gly His Asn Gln Leu
                100                 105                 110

Val Tyr Lys Leu Arg Asn Asp Asn Arg Val Val Ser Ile Glu Asp Phe
            115                 120                 125

Asn Ala Lys Asp Ile Asn Lys Glu Met Phe Asn Asp Glu Ile Pro Ser
130                 135                 140

Val Ile Val Ser Asp Val Ser Phe Ile Ser Ile Thr Lys Ile Ala Pro
145                 150                 155                 160

Ile Ile Phe Lys Glu Leu Asn Asn Leu Glu Phe Trp Val Thr Leu Ile
                165                 170                 175

Lys Pro Gln Phe Glu Ala Glu Arg Gly Asp Val Ser Lys Gly Gly Ile
                180                 185                 190

Ile Arg Asp Asp Ile Leu Arg Glu Lys Ile Leu Asn Asn Ala Ile Ser
            195                 200                 205

Lys Ile Ile Asp Cys Gly Phe Lys Glu Val Asn Arg Thr Ile Ser Pro
    210                 215                 220

Ile Lys Gly Ala Lys Gly Asn Ile Glu Tyr Leu Ala His Phe Ile Ile
225                 230                 235                 240
```

SERPULINA HYODYSENTERIAE VACCINE COMPRISING A TLY GENE MUTANT

This application is a continuation of U.S. patent application Ser. No. 08/950,433, filed Oct. 15, 1997 (which issued as U.S. Pat. No. 5,882,655 on Mar. 10, 1999), which, in turn, is a continuation of U.S. patent application Ser. No. 08/461,748, filed Jun. 5, 1995 (now abandoned), which, in turn, is a continuation of U.S. patent application Ser. No. 08/194,127, filed Feb. 9, 1994 (now abandoned), which, in turn, is a continuation of U.S. patent application 07/996,197, filed Dec. 23, 1992 (now abandoned), which claims priority to foreign application number EP 91203384.2, filed on Dec. 23, 1991 under35 U.S.C. 119.

The present invention is concerned with a vaccine for combating *Serpulina* (*Treponema*) *hyodysenteriae* infection and with recombinant polynucleotides and *Serpulina hyodysenteriae* mutants for the preparation of such a vaccine.

*Serpulina hyodysenteriae*, the major etiological agent of swine dysentery is an anaerobic, β-hemolytic spirochete found in the porcine large intestine. The disease is characterized by a mucohemorrhagic diarrhoea. This seems to be associated with the extensive superficial necrosis of the luminal epithelial lining and of the crypts of Lieberkuhn.

The disease leads to dehydration, weight loss and eventually death.

This pathogen secretes hemolysin which is thought to play an essential role in the pathogenesis of the disease.

*Serpulina hyodysenteriae* is differentiated from the non-pathogenic, weakly β-hemolytic *Serpulina innocens* by its hemolytic pattern on blood agar plates, or by testing enteropathogenicity in pigs or mice.

In vivo, during the acute disease course, up till now no immunogenic response induced by hemolysin could be serologically demonstrated.

Genetic approaches to elucidate the pathogenesis of spirochaetal infections have been hampered since a genetic exchange system permitting introduction of genes into spirochetal cells was absent. No methods of transformation or general transduction have been previously described.

According to the present invention, a vaccine can be prepared containing a mutant *Serpulina hyodysenteriae* which is defective in its production of biologically active hemolysin.

The mutation by which *Serpulina hyodysenteriae* is made defective in its production of biologically active hemolysin is established by means of genetical engineering techniques. Such mutations comprise e.g. deletion of part or the entire gene encoding hemolysin and/or nucleotide sequences controling the production of hemolysin, or insertion of an extra nucleotide or polynucleotide into the gene encoding hemolysin and/or the nucleotide sequences controling the production of hemolysin, or a combination of said deletion and insertion. The extra polynucleotide used for said insertion may be either a natural polynucleotide fragment derived from *Serpulina hyodysenteriae* or an other organism, or an unnatural polynucleotide. The extra polynucleotide may encode a foreign protein which is expressed by the treponeme, and which might be a protein useful in the selection of the mutant and/or may be a protein characteristic for and providing immunity against *Serpulina hyodysenteriae* or an other organism. Alternatively, the extra nucleotide or polynucleotide may serve merely to cause a frame shift in the hemolysin gene, thus resulting in abolishment of the production of biologically active hemolysin.

Genetical engineering methods which can be applied in establishing a mutation in *Serpulina hyodysenteriae* that results in abolishment of hemolysin production are known in the art for analogous approaches in other organisms.

An insertion can e.g. be established by first isolating the gene encoding hemolysin of *Serpulina hyodysenteriae*, inserting the extra nucleotide or polynucleotide into a suitable region of the coding or controling part of said gene and transforming the *Serpulina hyodysenteriae* with said mutated gene, thereby establishing recombination of at least part of the isolated gene with the chromosome of *Serpulina hyodysenteriae* Thereafter the *Serpulina hyodysenteriae* bacteria wherein hemolysin production is made defective are selected.

Preferably use is made of a self-replicating construct (plasmid, phage, etc.) harboring hemolysin. Prior to insertion of the extra nucleotide or polynucleotide, the gene encoding hemolysin is treated with restriction endonuclease, preferably having specificity for a restriction site which is unique in the construct. In order to be effectively ligated into the hemolysin gene, the insert should have 3' and/or 5' ends which are complementary or which are made complementary to the two ends in the hemolysin gene at the site of insertion.

Transformation of the *Serpulina hyodysenteriae* can be established by electroporation.

Genetically engineered *Serpulina hyodysenteriae* according to the present invention is useful in the prevention or combatment of Serpulina infections in susceptible individuals, in particular in swine. To this end use is made of a vaccine which contains and immunologically adequate amount of said genetically engineered Serpulina in live or inactivated form in a suitable carrier such as a buffer or the culture medium of the cells, optionally in the presence of one or more preservative constituents. In order to prepare a vaccine form which is more stable on storage, the Serpulina may be freeze-dried, optionally in the presence of one or more stabilizing constituents. Prior to use, the freeze-dried vaccine can be reconstituted by the addition of a carrier such as water or a buffer.

The vaccine may additionally contain other immunogens for swines, such as immunogenic material characteristic of viruses such as pseudorabies virus, influenza virus, transmissible gastroenteritis virus, parvo virus, porcine endemic diarhoea virus, hog cholera virus, or immunogenic material characteristic of mycoplasms, such as *Mycoplasma hyopneumoniae* and *Mycoplasma lyorhinis*, or immunogenic material characteristic of bacteria, such as *Escherichia coli*, *Bordetella bronchiseptica*, Leptospira, *Actinobaccilus pleuropneumoniae*, *Pasteurella multocida*, *Streptococcus suis*.

BRIEF DESCRIPTION OF THE DRAWINGS

FIG. 2A shows hybridization of Mutl strain DNA with a Tly probe. FIG. 2B shows hybridization of Mutl strain DNA hybridization with the Kana probe but no hybridization with WtC5. FIG. 2C shows no hybridization with DNA from Mutl or WtC5 strains with the BS probe.

EXAMPLE 1

CLONING OF A HEMOLYSIN GENE OF *SERPULINA HYODYSENTERIAE*

Materials and Methods

Figure 1:
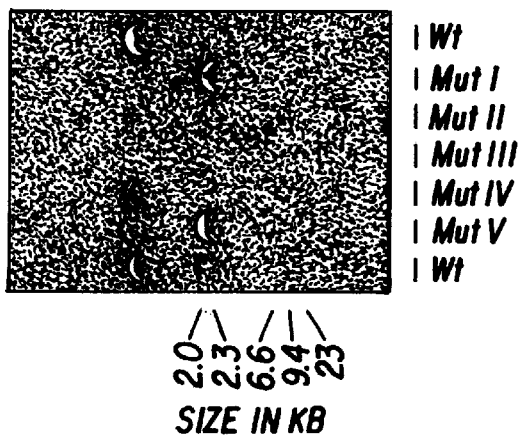
FIG. 1 shows the analysis of the PCR products of Serpulina hyodysenteriase by agarose gel electrophoresis.

Bacterial and Culture Conditions.

Use was made of the *Serpulina hyodysenteriae* strain B204 (serotype 2) attenuated through 124 consecutive passages. The Serpulinas were grown in trypticase soy medium (Difco Laboratories, Detroit, Mich., USA) supplemented with 5% FCS (Flow) as described by Halter and Joens (1988; Infec. Immun. 56, 3152–3156). Bacterial cell pellets were washed in TE and frozen at −70° C. The plasmid pUC 19 and the phagemids pBluescript pKS+ and pSK+ (Stratagene Cloning Systems, La Jolla, Calif., USA) were utilized for the cloning procedures. Escherichia coli (E. coli) K12 strain DH5-α(Gibco BRL, Gaithersburg, Md., USA) was used as a host for these vectors.

Pregaration of Serpulina hyodysenteriae Chromosomal DNA

Molecular-grade chemicals and enzymes were from Sigma Chemical Co. (St. Louis, Mo. USA). Frozen bacterial cell pellets from 1 liter cultures were thawed in 25 ml buffer containing 100 mmol/l Tris-HCI pH 8.0, 100 mmol/l EDTA, 150 mmol/l NaCI, and 10 mg/ml lysozyme. Following a 1 hour incubation at 37° C. 0.5 ml of RNAaseA was added to the cells which were then incubated an additional 15 minutes at 70° C. Cell lysis was completed by the addition of 2.5 ml of 30% Sarkosyl, gently mixing, and incubating at 70° C. for 20 minutes followed by a 1 hour incubation at 37° C. Predigested pronase, (final concentration of 10 mg/ml) was added and incubation continued for 4 hours at 37° C. The lysate was transferred to dialysis tubing and dialyzed overnight in 6 liters of TE (10 mmol/l Tris-HCI), 1 mmol/l EDTA, pH 8.0. The DNA was then once gently extracted with TE saturated phenol, extracted with chloroform:isoamyl alcohol (24:1), dialyzed for 6 hours in TE, and ethanol precipitated. Chromosomal DNA was resuspended in TE at a concentration of 1 mg/ml. DNA prepared in this manner was used for library construction and Southern blot analysis.

Construction of Serpulina hyodysenteriae Genomic Library

Restriction enzymes, calf intestinal phosphatase, T4 DNA ligase, RNAaseA, and Klenow fragment were obtained from Boehringer Mannheim Biochemicals (Indianapolis, Ind., USA). All enzymes were used under the conditions specified by the manufacturer. Standard cloning protocols (Maniatis, T. E. F. Fritsch, and J. Sambrook. 1982. Molecular Cloning: a laboratory manual. Cold Spring Harbor Laboratory, Cold Spring Harbor, N.Y., USA) were followed for all DNA manipulations. Serpulina hyodysenteriae DNA was digested with the restriction enzyme MboI and ligated with T4 DNA ligase to BamHI restricted, dephosphorylated pUCI9. E. coli DH5-α cells were transformed with the ligation mix and recombinants screened for hemolysin production.

Screening for Hemolytic Clones

Recombinants were plated on trypicase soy agar containing 4% defibrinated sheep red blood cells (SRBC) (Colorado Serum Co., Denver, Colo., USA) and 100 ug/ml carbenicillin (TSA blood plates). Plates were incubated at 37° C. for 24–36 hours to detect hemolytic colonies. A single hemolytic clone, designated pSML2, was chosen for further analysis. From this clone subclones were constructed.

Southern Blotting

Chromosomal DNA was digested with the restriction enzyme EcoRV, electrophoresed in a 0.8% agarose gel, and transferred to a nylon membrane. A 1.5 kbp ScaI/BamHI fragment from pJBA, the smallest subclone of pSML2 containing the active hemolysin gene, was random primer labeled with $^{32}P$ (Feinborg, A. P., and B. Vogelstein. 1983. A technique for radiolabelling DNA restriction endonuclease fragments to high specificity; Anal. Biochem. 1 32: 6–13). Prehybridization, hybridization and washing of the membrane were at 60° C. essentially as described (Maniatis, T., E. F. Fritsch and J. Sambrook. 1982. Molecular Cloning: a laboratory manual. Cold Spring Harbor Laboratory, Cold Spring Harbor, N.Y., USA). The membrane was exposed to Kodak X-OMAT AR film at −70° C. for periods of 2 to 18 hours.

Osmotic Release of the Recombinant Hemolysin

To characterize the recombinant hemolysin, E. coli DH5α (pJBA) cells were subjected to osmotic shock essentially as described by Heppel (Heppel, L. A. 1967. Selective release of enzymes from bacteria. Science 156:1451–1455).

Hemolysin Assays

Aliquots of the osmotic shock supernatants were adjusted to a final concentration of 140 mmol/l NaCI and added to sheep red blood cells (SRBC) which were washed and resuspended at 10% in 140 mmol/l NaCI. The mixtures were incubated at 37° C. for one hour and the release of hemoglobin from the red cells was determined by reading the optical density of the supernatant at 540 nm.

Extraction of Hemolysin from the Native Organism

Hemolysin was extracted from strain B204 using an RNA core extraction procedure (Kent, K. A., R. M. Lemeke, and R. J. Lysons. 1988. Production, purification and molecular weight determination of the haemolysin of Serpulina hyodysenteriae. J. Mod. Microbiol. 27:215–224) and concentrated.

Cytotoxity Assays

Osmotic shock supernatant from E. coli DH5α(pJBA), DH5a(pSML5) and DH5α(pUC19), and RNA core-hemolysin were filter- sterilized and added to $5 \times 10^4$ Chinese Hamster Ovary (CHO) cells/well as two-fold dilutions from 1:2 to 1:160. Cells were incubated at 37° C. for 24 hours in a $CO_2$ incubator and examined at various time intervals for cytopathic effect (CPE). CPE was determined by direct visual inspection of the CHO monolayer at 1, 12, and 24 hours following the addition of hemolysin to each well.

DNA Sequencing

The 1,5 kbp ScaI/BamHI insert in pJBA was subcloned into M13mpl8 and M13mp19. Both strands were sequenced by dideoxynucleotide chain termination using a Sequenase kit (United State Biochemical, Cleveland, Ohio). The -40MI3 sequencing primer was used to ascertain the sites of insertion and the first one hundred bases at the 3' and 5' regions of the gene. Subsequently, based on previous sequence, oligonucleotide primers synthesized on a Cyclone Plus DNA synthesizer (Millipore Corp., Bedford, Mass., USA) were used to sequence the complete hemolysin gene.

Results

Cloning of the Hemolysin Gene

The plasmid vector pUC 19 was utilized to prepare a library of Serpulina hyodysenteriae strain B 204. Plasmid DNA from the hemolytic clone, pSML2, contained a 5 kb fragment of Serpulina hyodysenteriae. The EcoR1(E)

subclone, pSML4, contained a 3.3 kb fragment and was as hemolytic as the parent plasmid pSML2. Digestion of pSML4 with ScaI/BamHI(S:ScaI) produced a 1.5 kb fragment which, when subcloned into EcoRV/BamHI restricted pBluescript phagemid pKS+ or pSK+, yielded the plasmid, pJBA, which was as hemolytic as either pSML2 or pSML4. The plasmid pJBA$^{KS}$ in *E. coli* JM105 was deposited with the Centraalbureau voor Schimmelcultures at Baarn, The Netherlands under deposit number No. 512.91.

Sequence of Hemolysin

The hemolysin gene was exceptionally adenosine-plus-thymidine rich (75%) as has been reported for pathogenic and non-pathogenic strains of Serpulinas (Miao, R. M., A. H. Fieldsteel, and D. L. Harris. 1970. Genetics of Treponema: characterization of *Treponema hyodysenteriae* and its relationship to *Treponema pallidum*. Infect. Immun. 22: 736–739). The sequence is shown in SEQUENCE ID NO. 1.

EXAMPLE 2

PREPARATION OF A *SERPULINA HYODYSENTERIAE* INSERTION MUTANT

Materials Aterials and Methods

Bacterial Strains and Plasmid

*Serpulina hyodysenteriae* C5 (deposited on Dec. 18, 1991 at the Centraalbureau voor Schimmelcultures at Baarn, the Netherlands under deposit number CBS 837.91) is cultured under the same conditions as described in Example 1 for the strain B204. The vector pBluescript II KS(+) was purchased from Stratagene (La Jolla, Calif.) and grown in *E.coli* K12 DH5α. Mice cecal contents were plated on media as described before.

Construction of a Hemolysin Gene Containing a Kanamycin Resistance Gene

For the construction of a hemolysin negative mutant use was made of plasmid PJBA$^{KS}$, containing the 1.5 kb ScaI/BamHI fragment including the hemolysin gene (further indicated as tly) of *Serpulina hyodysenteriae* B204 with a unique BglII site. A 1.3 kb Kanamycin Resistance GenBlock (EcoR1) (Pharmacia) was digested with the restriction enzyme BamHI and was inserted into this BglII site. The resulting $PJBA^{KS}$ derivative was named pTly-.

Electroporation

*Serpulina hyodysenteriae* C5 was grown in 200 ml trypticase soy broth (TSB), supplemented with 5% fetal calf serum and 0.05% RNA core, for 48 hours at 42° C. under anaerobic conditions. Cells were centrifuged, washed and harvested in 50 ml of icecold 15% glycerol-272 mM sucrose, centrifuged and resuspended to $10^{10}$ cells/ml in the same medium. Aliquots were frozen and kept at −80° C. until used. 50 μl of cell suspension was mixed with 5 μg of DNA in water. Electroporation was performed with a Bio-Rad Gene Pulser with pulse controller in 0.56 mm gap cuvettes (Biotechnologies and Experimental Research Inc., San Diego, Calif.) at 0.6kV, 25 μF and 200 Ω. This leads to time constants ranging from 3.5 to 4 ms. Cells were recovered in 1 ml TSB and poured onto trypticase soy agarplates, supplemented with 5% sheep blood and 400 μg of spectinomycin per ml (TSAB+). After 8 and 14 h of regeneration at 42° C. under anaerobic conditions, cells were harvested, plated onto TSAB+ agar plates supplemented with 30 or 150 μg/ml kanamycin and grown for 4 days at 42° C. under anaerobic conditions. Colonies were screened for diminished hemolysis. The electroporation experiments were carried out in duplicate.

Polymerase Chain Reaction

Colonies with diminished hemolysis detected after electroporation, and wildtype (Wt) *Serpulina hyodysenteriae* C5 were screened with polymerase chain reaction (PCR). DNA amplification with Taq polymerase and Taq polymerase buffer (Promega) was performed with primers corresponding to nucleotides 471–486 and 1449–1431 of the pJBA Sequence ID No. 1. This resulted in an amplified product of 0.98 kb of the tly gene including the BglII site. For the Wt C5, 0,5 μg DNA was used. Colonies of the mutants were touched with a sterile toothpick and transferred to the PCR buffer. After the mixtures were preheated at 95° C. for 3 minutes, 35 amplification cycles were performed in a DNA Incubator Prem, as follows: 1 min at 95° C., 1 min at 40° C. and 2 min at 72° C. After the final cycle, the mixture was incubated for 10 min at 72° C. to complete the last polymerase reaction. Reaction mixtures were analyzed by agarose gel electrophoresis as described before.

Isolation of DNA and Southern Blot Analysis

Plasmid DNA was isolated from *E.coli* and *Serpulina hyodysenteriae* by the method of Birnboim and Doly (Nucleic Acids Research 7, 1513–1523; 1989). Chromosomal DNA of *Serpulina hyodysenteriae* was isolated by isopropanol precipitation and phenol extraction. DNA was digested with EcoRV as indicated by the supplier (BRL). EcoRI digests of pBluescript II KS(+) and a pBluescript II KS(+)/Kanamycin Resistance Genblock construct were taken as controls. Hybridization on Hybond N (Amersham) and washing was performed as described before. The 1.5 kb ScaI/BamHI fragment of $pJBA^{KS}$ (Tly probe), the 1.3 kb Kanamycin Resistance Genblock (Pharmacia) (Kana probe) and the complete vector Bluescript (BS probe) were radiolabeled and used as probes.

Virulence Test in Mice

The mouse challenge studies were done as described before. Six week old female OF-1 mice (Iffa Credo) were kept under controlled conditions. Feed was removed 14 h before the first challenge and was withheld for 40 hours. Mice were administered two consecutive doses (24 h apart) by gastric intubation with 0.5 ml of a log-phase culture of serpulinas: $10^6$ or $10^{8\ CFU}$ *Serpulina hyodysenteriae* Wt C5, $10^6$ or $10^8$ CFU *Serpulina hyodysenteriae* C5 tly-, or $10^8$ CFU *Serpulina innocens* ATCC 29796. Three control mice were inoculated with 0.5 ml TSB. The mice were necropsied 12 days later to evaluate signs of *Serpulina hyodysenteriae* infection in the cecum: catarrhal inflammation, excess intraluminal mucus, oedema, hyperemia and atrophy. Cecal contents were cultured to assay shedding of serpulinas.

Results

Electroporation

In two separate experiments with the pTly construct, a total of 5 kanamycin resistant colonies with diminished hemolysis were recovered. In the first experiment, when cells were plated on TSAB+ plates with only 30 μg/ml kanamycin, one less hemolytic colony (MutI) was recovered among many strong hemolytic colonies. In the second experiment, when cells were plated on TSAB+ plates with 150 μg/ml kanamycin, 4 colonies with diminished hemolysis (MutII-V) were found.

Polymerase Chain Reaction

Upon analysis of the PCR products of *Serpulina hyodysenteriae* Wt C5 and MutI-MutV by agarose gel electrophoresis, Wt C5 and MutIV showed a fragment of only 0.98 kb, which is the expected size of the fragment of the tly gene amplified by the primers of pJBA used. MutI, MutII, MutIII and MutV showed a fragment of 2.28 kb (0.98 kb of the tly gene and 1.30 kb of the kanamycin gene block) (FIG. 1; molecular size markers in kilobase pairs (kb) are given on the right hand side of this figure).

DNA Isolation and Southern Blot Analysis

Figure 2:
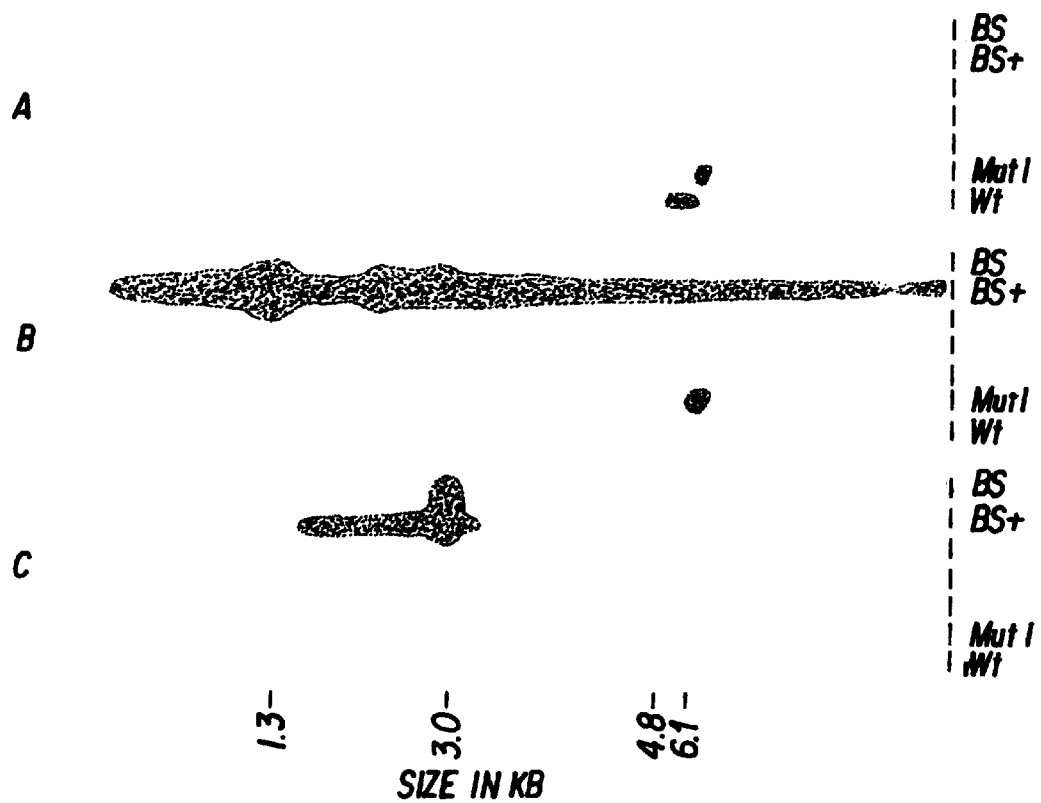
FIGS. 2A–C show DNA isolation and southern blot analysis.

No plasmid DNA could be isolated from the mutants MutI-V. Chromosomal DNA of *Serpulina hyodysenteriae* Wt C5 and MutI-V was digested with EcoRV, blotted and hybridized with the Tly probe, Kana probe and BS probe respectively. In strain Wt C5 the Tly probe hybridized with a fragment of 4.8 kb. In MutI this probe hybridized with a fragment of 6.1 kb (i.e. 4.8 kb plus 1.3 kb kanamycin gene insertion) (FIG. 2A). Strain Wt C5 did not hybridize with the Kana probe. A fragment of 6.1 kb in MutI hybridized with the Kana probe (FIG. 2B). Neither MutI nor WtC5 hybridized with the BS probe (FIG. 2C).

Virulence Test of MutI in Mice

Six groups of OF-1 mice were challenged with $10^6$ or $10^8$ CFU of *Serpulina hyodysenteriae* Wt C5, $10^6$ or $10^8$ CFU of MutI, $10^8$ CFU of Serpulina innocens ATCC 29796, or TSB (controls). Mice were killed at day 12 for evaluation of cecal lesions (catarrhal inflammation, excess intraluminal mucus, oedema, hyperemia and atrophy) and colonization by serpulinas. Cecal scores are represented in Table 1. Macroscopic cecal lesions were scored as follows: severe lesions, 3; moderate lesions, 2; mild lesions, 1; no lesions, 0. Macroscopic cecal lesions were less severe in mice infected with MutI (both inoculation doses) than in mice infected with *Seruplina hyodysenteriae* Wt C5. Mice infected with *Serpulina innocens* or inoculated with TSB, did not show any cecal lesions. The number of mice that were culture positive, are also shown in Table 1. In the group infected with *Serpulina innocens*, no mouse was culture positive.

TABLE 1

| group mice[e] | CFU | n[f] | group mean cecal score | number of mice lesion positive | number of mice culture positive |
|---|---|---|---|---|---|
| Wt C5 | $10^8$ | 7 | 2.42 | 7 | 7 |
| Wt C5 | $10^6$ | 6 | 1.66 | 6 | 5 |
| MutI | $10^8$ | 7 | 1.28 | 5 | 7 |
| MutI | $10^6$ | 7 | 1.00 | 5 | 4 |
| S.inno[c] | $10^8$ | 7 | 0 | 0 | 0 |
| TSB | | 3 | 0 | 0 | 0 |

[a]*Serpulina hyodysenteriae* C5 wildtype
[b]MutI = hemolysin tly-mutant of *Serpulina hyodysenteriae* C5
[c]S.inno = *Serpulina innocens* American Type culture Collection (ATCC) 29796
[d]TSB = trypticase soy broth
[e]female SPF OF-1 mice (lffa Credo)
[f]n = number of mice per group
[g]cecal score: macroscopic cecal lesions were scored as follows: severe lesions, 3; moderate lesions, 2; mild lesions, 1; no lesions, 0.

---

We claim:

1. An isolated and purified mutant strain of *Serpulina hyodysenteriae* capable of eliciting an immune response against a wild-type virulent strain of *Serpulina hyodysenteriae* and that is less virulent than the wild-type strain, said mutant strain being generated by using a genetic engineering technique that abolishes the expression of hemolysin encoded by the chromosomal tly gene.

2. An isolated and purified mutant strain according to claim 1, wherein said genetic engineering technique comprises deleting a portion of the tly gene.

3. An isolated and purified mutant strain according to claim 1, wherein said genetic engineering technique comprises introducing an insertion mutation or a deletion mutation into the tly gene that results in a shift in the reading frame of the tly gene.

4. A vaccine containing the mutant strain of *Serpulina hyodysenteriae* according to claim 1 and a suitable carrier.

5. A vaccine containing the mutant strain of *Serpulina hyodysenteriae* according to claim 2 and a suitable carrier.

6. A vaccine containing the mutant strain of *Serpulina hyodysenteriae* according to claim 3 and a suitable carrier.

7. A vaccine according to claim 4, wherein the mutant strain is alive.

8. A method for reducing the severity of a *Serpulina hyodysenteriae* infection, comprising administering to a susceptible host the vaccine according to claim 4.

9. A method for reducing the severity of a *Serpulina hyodysenteriae* infection, comprising administering to a susceptible host the vaccine according to claim 5.

10. A method for reducing the severity of a *Serpulina hyodysenteriae* infection, comprising administering to a susceptible host the vaccine according to claim 6.

11. A method for reducing the severity of a *Serpulina hyodysenteriae* infection, comprising administering to a susceptible host the vaccine according to claim 7.

* * * * *